United States Patent [19]

Chang

[11] Patent Number: 4,902,312

[45] Date of Patent: Feb. 20, 1990

[54] CARBON MOLECULAR SIEVES FOR PURIFICATION OF CHLOROFLUOROCARBONS

[75] Inventor: Chin-Hsiung Chang, Palatine, Ill.

[73] Assignee: Allied-Signal Inc., Morris Township, Morris County, N.J.

[21] Appl. No.: 304,060

[22] Filed: Jan. 30, 1989

[51] Int. Cl.$^4$ ............................................. B01D 53/04
[52] U.S. Cl. ............................................. 55/71; 55/75
[58] Field of Search ............................ 55/71, 75, 389

[56] References Cited

U.S. PATENT DOCUMENTS

| | | | |
|---|---|---|---|
| 3,947,558 | 3/1976 | van Eijl | 423/483 |
| 3,976,447 | 8/1976 | Merchant et al. | 55/71 |
| 4,102,981 | 7/1978 | Weychanin et al. | 423/240 |
| 4,128,626 | 12/1978 | Merchant et al. | 423/488 |
| 4,820,318 | 4/1989 | Chang et al. | 55/71 X |

OTHER PUBLICATIONS

Juntgen et al., "Carbon molecular sieves: production from coal and application in gas separation", *FUEL*, 1981, vol. 60, Sep., pp. 817–822.

*Primary Examiner*—Robert Spitzer
*Attorney, Agent, or Firm*—Harold N. Wells; Jay P. Friedenson; Gerard P. Rooney

[57] ABSTRACT

Chlorofluorocarbons are purified by removing hydrofluoric and hydrochloric acids with a carbon molecular sieve having an average pore size of about 3.5 Angstroms with no more than about 5% of the pores having a size less than 3.2 Angstroms and no more than about 5% of the pores having a size greater than 4.2 Angstroms.

9 Claims, No Drawings

CARBON MOLECULAR SIEVES FOR PURIFICATION OF CHLOROFLUOROCARBONS

BACKGROUND OF THE INVENTION

The invention relates generally to the purification of chlorofluorocarbons. Such materials are frequently made by the reaction of hydrofluoric acid with chlorinated hydrocarbons so that the chlorine atoms are replaced with fluorine atoms. This process inherently produces byproduct hydrochloric acid while some hydrofluoric acid is left unreacted. Consequently, the fluorinated product must be purified. Typically, this has been done by distillation or similar steps. However, these are expensive and complex and simpler procedures are desirable. In addition, losses of the fluorinated product result.

Several U.S. patents deal with the general subject of removal of hydrogen fluoride from halogenated hydrocarbons. In particular, U.S. Pat. No. 4,128,626 discloses a method in which small amounts of hydrogen fluoride in a gas also containing hydrogen chloride are separated by contact with solid calcium chloride. It is indicated that this process has an application to the off gases from the fluorination of chlorinated hydrocarbons which is the general subject of the present invention.

Another approach is shown in U.S. Pat. No. 3,976,447 in which similar streams are scrubbed of their hydrogen fluoride content by contacting with a solid alkaline earth metal fluoride which has been prepared by fluorination of anhydrous calcium chloride. Such material is said to be regenerable and to have a high capacity for hydrogen fluoride.

Another method which employs a liquid rather than a solid absorbent is shown in U.S. Pat. No. 4,102,981 where hydrogen chloride is removed from halogenated hydrocarbons by scrubbing with an aqueous solution of trisodium phosphate and sodium hydroxide.

A substantially different technique is disclosed in U.S. Pat. No. 3,947,558 in which a liquid phase process for recovery of halogenated hydrocarbons employs a glycol to separate hydrogen fluoride from a liquid phase containing the desired halogenated hydrocarbons. In such a process it is anticipated that hydrogen chloride, which is a byproduct of the process for producing fluorinated hydrocarbons, will be separated first before the organic liquid phase is treated with a glycol to remove hydrogen fluoride.

It would be most desirable to find a method for purification of fluorinated hydrocarbons which would directly remove only the hydrochloric acid and hydrofluoric acid with essentially no loss of the valuable product, thus maximizing the yield while minimizing the waste which must be disposed of. If the acids could be recovered, then they could be sold or reused, again reducing to the waste disposal problems. The inventor has found a method for closely achieving these objectives.

SUMMARY OF THE INVENTION

A process for the purification of chlorofluorocarbons by removal of hydrofluoric and hydrochloric acids comprises passing said chlorofluorocarbons contaminated with said acids over a sufficient amount of a carbon molecular sieve having an average pore size of 3.5 Angstroms with no more than about 5% of the pores having a size less than 3.2 Angstroms and no more than about 5% of the pores having a size greater than 4.2 Angstroms. When a packed bed of adsorbent is used, the gas hourly space velocity will be about 50 to 1000 $hr^{-1}$, preferably about 200 to 500 $hr^{-1}$. The operating temperature generally will be in the range of $-20°$ to 80 degrees C, preferably about $-10°$ to $40°$ C. The pressure generally will be about 108 to 3550 kPa, preferably about 700 to 2000 kPa.

The preferred carbon molecular sieves used to purify fluorocarbons are prepared by a unique process comprising:

(a) polymerizing a cross-linking agent, preferably divinylbenzene, and a precursor monomer, preferably vinylidene chloride, with both the cross-linking agent and the monomer being essentially free of molecular oxygen, and producing a cross-linked polymer;

(b) shaping the polymer of (a) into the desired configuration without employing a binder;

(c) carbonizing the shaped polymer of (b) at a temperature above 800° C. in the substantial absence of oxygen.

DESCRIPTION OF THE PREFERRED EMBODIMENTS

Carbon Molecular Sieves

Carbon molecular sieves are available commercially. They are usually derived from natural sources such as coal. One example is the carbon molecular sieves described in a paper by Juntgen et al. of Bergbau-Forschung GmbH in FUEL, 1981, Vol. 60, September, p. 817-822.

The preferred carbon molecular sieves used for the purification of fluorocarbons are produced by a unique method. This method of manufacturing may be broadly characterized as comprising three steps: (1) polymerization of an oxygen-free monomer in the presence of an oxygen-free cross-linking agent; (2) forming particles of the resultant polymer into a desired shape; and then, (3) carbonizing the shaped material in a substantially oxygen-free environment.

The monomer can be chosen from a number of different monomers. They should be readily polymerizable, essentially free of oxygen in their molecular structure and preferably comprised basically of hydrogen, a halogen, and carbon. Among the materials which may be employed as the monomer are acrylonitrile (AN), vinylidene fluoride (PVDF), chlorotrifluoroethylene (HALAR), vinylidene chloride (PVDC), mixtures of two or more monomers such as mixtures of vinylidene chloride and vinyl chloride, vinylidene chloride and acrylonitrile, and a mixture of styrene and divinylbenzene. Other monomers which are suitable for utilization in the subject invention are vinyl fluoride, vinyl bromide, chlorinated ethylene, chlorofluorethylene, vinyl chlorobenzene, vinylidene bromide and vinylidene-fluoride-chlorotrifluoroethylene. The preferred monomer is vinylidene chloride.

Polymerization reactions may be performed according to a number of different procedures known in the art. However, the most favorable results have been obtained employing a bulk polymerization or a solution polymerization.

A bulk polymerization is the direct conversion of liquid monomer to polymer in a reaction system in which the polymer remains soluble in its own monomer. To remove the exothermic heat of polymerization this type of polymerization is often terminated at relatively low conversions of 40–60 percent and excess monomer drained and distilled off for use in subsequent polymerization. Solution polymerization is a method in which a solvent is used capable of dissolving the monomer, the polymer, and the polymerization initiator.

Suspension polymerization and emulsion polymerization do not produce materials having the same level of desired properties and therefore are less preferred methods of polymerization. In suspension polymerization, the monomer is dispersed rather than dissolved in the medium with water being a typical suspension medium. The initiator is dissolved in the monomer, the monomer is dispersed in water, and a dispersing agent is incorporated to stabilize the suspension formed. The monomer droplets are generally on the order of approximately 0.1–1.0 millimeter in size. In emulsion polymerization, the polymerization is within a suspended particle of colloidal size of approximately 50 to 1500 Angstroms in diameter. The initiator is normally found in the aqueous phase and not within the monomer. It is believed that precipitation polymerization and vapor phase polymerization would also be suitable.

The carbon molecular sieves prepared from bulk and solution polymerized precursors are hydrophobic whereas the precursors synthesized with various emulsion and suspension formulations produced carbon molecular sieves with hydrophilic characteristics. It is believed adjustment of the methods used to perform the emulsion and suspension polymerizations may result in the production of hydrophobic molecular sieves. The mechanism which causes the performance of the finished sieve to be dependent upon the method of polymerization employed is not understood. These differences may result from the inclusion within the polymer and therefore within the finished molecular sieve of the remnants of the materials required to form the suspension or added to the suspension for a number of purposes such as surfactants added to aid in the production of a desired emulsion.

Promoted cross-linking appears necessary. The polymers produced in the initial polymerization step should be cross-linked with a substantially oxygen-free cross-linking agent. The cross-linking agent will typically be present during the polymerization at a concentration equal to less than 10 mole percent of the monomer. A preferred cross-linking agent is divinylbenzene. Other cross-linking agents which are contemplated for use in the subject method include trivinyl benzene, divinyl acetylene, and divinyl sulfide.

As the production of carbon molecular sieves from polymers having a no-oxygen functionality is desired, the polymerization initiator is also preferably an oxygen-free compound. Therefore, a carbon or azo rather than an oxygen initiator is preferably used. One suitable non-oxygen containing initiator is 2,2'-azobis-(isobutyronitrile), (AIBN), which has a molecular formula of $C_8H_{12}N_4$. Another highly suitable polymerization initiator is the compound 2,2' azobis (2,4-dimethylvaleronitrile) which is available from DuPont Chemical Company and is sold under the trade VAZO 52. The formula of the latter compound is $C_{14}H_{24}N_4$. If the precursor polymer is produced by solution polymerization, a number of different solvents may be employed. Typical solvents include normal hexane, chloroform, carbon tetrachloride, orthodichlorobenzene, and 1,1,2,2-tetrachloroethane. Of these materials, orthodichlorobenzene and 1,1,2,2-tetrachloroethane appear to be preferable as they resulted in higher polymer yields. General characteristics for the selection of a solvent include a high-solubility for the monomer, the absence of oxygen from the molecular structure, and a large difference in boiling point between the solvent and the monomer. A weight ratio between monomer and solvent between 1:1 to 1:2 will normally be suitable.

The material formed by the polymerization may be obtained in a number of different forms such as one or more large masses formed within a reactor or a large number of smaller particles. For ease in fabricating the polymer into a desired shape it is preferably reduced in size to small free-flowing granules or powder. These granules are then shaped or formed into a desired configuration such as a cylinder. sphere, pellets, and the like. This shaping or forming may be done by conventional means familiar to those skilled in the art.

The shaped polymeric material is carbonized by heating the shaped material to a high temperature in an essentially oxygen-free environment. The concentration of oxygen in the atmosphere surrounding the particles undergoing carbonization should be less than 0.1 mole percent and preferably less than 0.05 mole percent. The carbonization will result in the evolution of a hydrogen halide. Preferably the inert gas should be flowing at a sufficient rate to remove this material from the particles. It is preferred that prior to high temperature carbonization the shaped polymer precursor material is subjected to a mild heating step during which its temperature is raised above 150° C., e.g. 240° C., and that the pellet is held at this temperature until no more weight loss occurs. The shaped material is then preferably subjected to a programmed temperature increase to a temperature above 700° C., preferably above 800° C., particularly, above 900° C. The temperature of the shaped precursor material is preferably raised at a rate greater than 50° C. per hour but less than 200° C. per hour preferably 75°–125° C. per hour. Also, it is preferred to hold the shaped material at the final high temperature, such as 800° C., for a period of at least 45 minutes and preferably for at least one hour.

The sieve precursors are derived from polymeric materials which are substantially free of the inorganic materials such as metals and inorganic oxides which may be present when the precursor material is made from a naturally occurring substance such as coal, coconut shells, peat, or wood. Materials which also contain a binder prior to carbonization will normally have impurities derived from the binder in addition to impurities present in the precursor materials. The preferred sieves, on a hydrogen- and oxygen-free basis, should contain at least 99.5 wt. % carbon and preferably at least 99.8 wt. % carbon.

While the just described method produces a unique and useful carbon molecular sieve, the average pore size is about 4.2 Angstroms and accordingly, it must be further treated to reduce the pore size to meet the critical size range discussed below. Various techniques may be used to reduce the pore size, such as the deposition of carbon with hydrocarbons at high temperature. Reference may be made to the paper by Juntgen et al. mentioned earlier in connection with commercially available molecular sieves made from natural sources. One preferred method is the deposition of carbon with toluene at about 800° C.

Purification of Chlorofluorocarbons

Chlorofluorocarbons are widely used and comprise a large group of compounds containing chlorine and fluorine atoms in various proportions as is well known to those skilled in the art. Generally such materials are produced by hydrofluorination of chlorocarbons and other chlorofluorocarbons using hydrogen fluoride in the presence of a catalyst. Thus, the desired product will contain both residual hydrogen fluoride and hydrogen chloride which is produced when a fluorine atom replaces a chlorine atom. Clearly, the aggressive nature of these acids makes their recovery by adsorption difficult. However, the carbon molecular sieves described above, which are preferred, as well as certain other carbon molecular sieves having the desired average pore size can be used to adsorb both hydrogen fluoride and hydrogen chloride and to separate the two acids.

The carbon molecular sieves which are useful in purification of chlorofluorocarbons have an average pore size of 3.5 Angstroms, but only very few larger or smaller pores. Specifically, the carbon molecular sieves should have no more than about 5% of the pores larger than 4.2 Angstroms and no more than about 5% smaller than 3.2 Angstroms. Providing such a narrow pore size range is critical to making the separation between HF and HCl and chlorofluorocarbons. It will be understood by those skilled in the art that measurement of average pore size is difficult, particularly where the pore size is deliberately reduced. Consequently, in many uses the average pore size is inferred from the separations which are observed.

Although various methods of contacting the impure chlorofluorocarbon with carbon molecular sieves are feasible, e.g. employing fluidized or moving beds, passing the chlorofluorocarbon over a fixed bed of carbon molecular sieve particles is preferred. In such a process the gas space velocity would be in the range of about 50 to 1000 hr$^{-1}$, preferably 200 to 500 hr$^{-1}$. The shape of the bed and the size of the particles will be determined by various factors familiar to those skilled in the art. The pressure generally could be between about 108 and 3550 kPa, but about 700 to 2000 kPa would be preferred. The temperature of the process will be about $-20°$ to $80°$ C., particularly $-10°$ to $40°$ C.

It has been found that carbon molecular sieves meeting the criteria described above can be regenerated by thermal and/or vacuum desorption, thus permitting the continuous use of a bed of carbon molecular sieves. Successful regeneration may be carried out by heating the bed to temperatures of about $120°$ to $160°$ C. and at pressures of about 6.5 to 33.6 kPa.

In the following examples refrigerant 22, chlorodifluoromethane, was used as a model compound. Specifically, Genetron® 22 (G-22), produced by Allied-Signal Inc. was used. HCl, HF, and $Cl_2$ were added to the G-22 and the impure chlorofluorocarbon passed over various carbon molecular sieves.

EXAMPLE 1

Comparative

A 0.2 gm sample of a carbon molecular sieve, obtained from Bergbau Forschung GmbH was modified by a toluene treatment at $750°$ C. to reduce the pore size. The sample was exposed to a series of single components at pressures of 44 torr of $Cl_2$, 42 torr of HCl, and 44 torr of G-22. The amount of each component adsorbed was found to be near equilibrium after about 40-50 minutes.

Adsorption of HCl, G-22, and $Cl_{12}$ was measured by a McBain balance, which is a gravimetric method for measuring the gas uptake under equilibrium conditions. The amount of each component adsorbed was:

TABLE 1

| Component | mmol/gm adsorbent | gm/gm adsorbent |
|---|---|---|
| $Cl_2$ | 2.7 | 0.194 |
| HCl | 2.2 | 0.080 |
| G-22 | 0.7 | 0.056 |

It may be concluded that while this molecular sieve could be used to adsorb $Cl_2$ and HCl it would adsorb an undesirable amount of G-22, leading to losses of G-22 and impure $Cl_2$ and HCl recovered. Thus the average pore size is believed to be about 4.2 Angstroms.

EXAMPLE 2

In another experiment carried out as in Example 1, another carbon molecular sieve obtained from Kaldair was exposed to HCl, $Cl_2$ and G-22 at various pressures. The results of three such experiments are given below:

TABLE 2

| | gm/gm adsorbent | | |
|---|---|---|---|
| Test No. | HCl | $Cl_2$ | G-22 |
| 1 | 0.12.9(a) | 0 | 0 |
| 2 | 0.108(a) | 0 | 0 |
| 3 | 0.081(b) | | |
| 4 | 0.118(c) | N/A | N/A |

(a) 200 torr
(b) 100 torr
(c) 600 torr

It may be concluded that this carbon molecular sieve would be more suitable for separating HCl from G-22 in the presence of $Cl_2$ than the carbon molecular sieve of Example 1. Thus, the average pore size is believed to be about 3.5 Angstroms.

EXAMPLE 3

In another experiment carried out as in Example 1 a third carbon molecular sieve obtained from Bergbau Forschung GmbH was modified by treatment with toluene at $750°$ C. to reduce the average pore size. The sample was tested for its ability to adsorb HCl, $Cl_2$ and G-22, at pressures of 47 torr, 47 torr, and 49 torr, respectively. Less than 0.1 mmol of $Cl_2$ or G-22 was absorbed per gm of adsorbent (about 0.004 gm/gm). HCl was adsorbed at about 1.6 mmol/gm at equilibrium (about 0.058 gm/gm). It may be concluded that HCl could be selectively recovered in the presence of $Cl_2$ and HCl. Consequently, it is believed that the average pore size is about 3.2 Angstroms.

EXAMPLE 4

A G-22 stream was passed at 180 mL/min over a 45 gm sample of the carbon molecular sieve used in Example 3 for about 22 minutes with no indication of adsorption of the G-22. Then 200 mL/min of a G-22 stream containing 11.5 vol. % HCl and 37.3 vol. % HF was passed over the carbon molecular sieve. The outlet of the adsorbent bed was analyzed by gas chromatography. After about 28 minutes, breakthrough began. The concentration of HCl in the outlet gas rose to about 53% HCl after about 55 minutes and continued until about 120 minutes, after which the HCl concentration fell and stabilized at about 20%. Analysis for HF in the effluent gas showed that no HF was detected until about 120 minutes had elapsed, when HF broke through and reached about 30% after about 140 minutes. It may be concluded that it would be possible to selectively separate HCl and HF from G-22.

EXAMPLE 5

In another dynamic test a feed stream containing 50 vol. % HCl, 40 vol. % G-22, and 7.5 vol. % HF was passed over a 6.0 gm sample of the carbon molecular sieve of Example 2 at a flow rate of 50 mL/min. Analysis of the effluent gas showed complete adsorption of HCl for about 10 minutes, after which a breakthrough occurred. HF was not detected until about 140 minutes had elapsed.

EXAMPLE 6

The previous dynamic tests were run at about room temperature. In an experiment similar to Example 5, the temperature was lowered to −5.6° C. with similar results being obtained.

EXAMPLE 7

A 44.8 gm sample of the carbon molecular sieve of Example 2 which was saturated with HCl and HF was regenerated by passing a stream of 200 mL/min of helium over it at 140° C. Analysis of the effluent gases indicated that complete removal of HCl and HF was obtained and the original capacity of the carbon molecular sieve was restored.

EXAMPLE 8

A carbon molecular sieve was prepared by the preferred methods described earlier, using vinylidene chloride as the monomer and divinylbenzene as the cross-linking agent, in a mol ratio of 99.5/0.5. The average pore size as prepared was about 4.2 Angstroms but this was reduced to about 3.5 Angstroms by exposing the carbon molecular sieve to toluene at a temperature of 800° C. The test described in Example 1 was carried out with pressures of 23.8 torr for $Cl_2$ and 31.5 torr for G-22. After equilibrium was reached, it was found that 7.8 mmol of $Cl_2$ had been adsorbed for each gram of the carbon molecular sieve; while 2.3 mmol of G-22 had been absorbed for each gram.

EXAMPLE 9

Carbon molecular sieves may be treated with steam, air, or carbon dioxide to increase the average pore size. The effect of such a treatment as shown in the following table which reports the absorption capacity of a carbon molecular sieve from Kaldair using the static test described in Example 1. Each sample was treated by being exposed to steam at atmospheric pressure and the designated temperature.

| Effects of Steaming on the Adsorption of Kaldair Carbon | | | | | | |
|---|---|---|---|---|---|---|
| Steam Treatment Conditions | | | Adsorption Capacity (%, g/g) | | | |
| | | | Cl2 | | G-22 | |
| Temp (°C.) | Time (min) | wt. Loss (%) | P (torr) | Loading (g) | P (torr) | Loading (g) |
| 700 | 18 | 2.9 | 32 | 0.5 | — | — |
| 800 | 18 | 5.8 | 28 | 14.8 | 46 | 11.6 |
| 850 | 20 | 16.4 | 28 | 26.0 | 46 | 12.8 |

It will be evident that increasing the steam temperature markedly increased the weight loss, capacity for both chlorine and G-22 was greatly increased as well. It may be concluded that the pore size was too great to permit an efficient separation of chlorine and G-22. The average pore size is concluded to be greater than about 4.2 Angstroms.

EXAMPLE 10

Carbon molecular sieves may be treated with hydrocarbons at high temperatures to deposit carbon by a cracking of the hydrocarbon molecules. The effect of such a treatment is shown in the following table which reports the capacity of a carbon molecular sieve from Bergbau-Forschung GmH using the static test described in Example 1. Each sample was treated by exposure to toluene at atmospheric pressure and the designated temperatures.

| Effects of Toluene Modification on the Adsorption on Bergbau Forschung Carbon (4) | | | | | | |
|---|---|---|---|---|---|---|
| Treatment Condition | | HCl | | Cl2 | | G-22 |
| Temp (°C.) | Time (min) | P (torr) | Capacity | P (torr) | Capacity | P (torr) | Capacity |
| None (Control) | — | 52.1 | 7.74 | — | — | 44.2 | 16.59 |
| 700 | 15 | 46.8 | 6.11 | 44.2 | 3.13 | 44.2 | 1.72 |
| 750 | 15 | 46.8 | 5.88 | 46.8 | 0.45 | 49.5 | 0.30 |
| 800 | 16 | 44.2 | 1.95 | 54.7 | 0.16 | 44.2 | 0 |

It will be noted that while the initial carbon molecular sieve had significant capacity for HCl, $Cl_2$, and G-22 and thus would not be useful for separating these compounds, that the relative capacity for HCl versus $Cl_2$ and G-22 was changed by decreasing the average pore size so that a treatment at 800° C. provided a carbon molecular sieve which could separate HCl from $Cl_2$ and G-22.

I claim:

1. A process for the removal of hydrofluoric and hydrochloric acids from chlorofluorocarbons comprising contacting said chlorofluorocarbons at removal conditions with a sufficient amount of a carbon molecular sieve having an average pore size of about 3.5 Angstroms with no more than about 5% of the pores having a size less than 3.2 Angstroms and no more than about 5% of the pores having a size greater than 4.2 Angstroms.

2. The process of claim 1 wherein said carbon molecular sieve is disposed as a fixed bed and said chlorofluorocarbons are passed over said bed with a gas hourly space velocity of about 50 to 1000 $hr^{-1}$.

3. The process of claim 1 wherein said contacting is carried out at a temperature of about −20° to 80° C. and at a pressure of about 108 to 3550 kPa.

4. The process of claim 1 wherein said carbon molecular sieves are manufactured by the method comprising the steps of:
 (a) polymerizing a cross-linking agent and a precursor monomer, with both the cross-linking agent and the monomer being essentially free of molecular oxygen, and producing a cross-linked polymer;
 (b) shaping a quantity of the polymer into an article having the desired configuration without employing a binder material; and,
 (c) carbonizing the resultant shaped article into a finished product comprising carbon molecular sieves and having the same overall shape as the article.

5. The process of claim 4 wherein the carbonization step is carried out in the substantial absence of oxygen at a temperature above 800° C.

6. The process of claim 4 wherein a bulk or solution method of polymerization is employed in step (a).

7. The process of claim 4 wherein said cross-linking agent is divinyl benzene and said monomer is vinylidene chloride.

8. The process of claim 4 wherein the average pore size of the finished carbon molecular sieves of (c) is reduced by treatment with hydrocarbons at high temperatures.

9. The process of claim 8 wherein said hydrocarbon is toluene and said temperature is about 800° C.

* * * * *